(12) United States Patent
Hildt et al.

(10) Patent No.: US 7,262,267 B1
(45) Date of Patent: Aug. 28, 2007

(54) POLYPEPTIDE MEDIATING CELL PERMEABILITY

(75) Inventors: Eberhard Hildt, Berlin (DE); Stephanie Schmidt, Frankfurt (DE)

(73) Assignee: Island Pharmacueticals, Ltd., Isle of Man, British Isles ( * ) Notice: Subject to any disclaimer, the term of this patent is extended or adjusted under 35 U.S.C. 154(b) by 0 days.

(21) Appl. No.: 09/830,981

(22) PCT Filed: Nov. 3, 1999

(86) PCT No.: PCT/DE99/03506

§ 371 (c)(1), (2), (4) Date: Oct. 29, 2001

(87) PCT Pub. No.: WO00/26379

PCT Pub. Date: May 11, 2000

(30) Foreign Application Priority Data

Nov. 3, 1998 (DE) ................. 198 50 718

(51) Int. Cl.
*A61K 38/04* (2006.01)
*A61K 38/17* (2006.01)

(52) U.S. Cl. ...................... 530/300; 530/350

(58) Field of Classification Search ........... 530/300, 530/350
See application file for complete search history.

(56) References Cited

FOREIGN PATENT DOCUMENTS

| DE | 19808258 | * 9/1998 |
|---|---|---|
| EP | 0 456 215 | 11/1991 |
| WO | 95 20657 | 8/1995 |
| WO | WO 98/50426 | * 11/1998 |
| WO | WO 00/46376 | 8/2000 |

OTHER PUBLICATIONS

Wieprecht et al., Biochemistry 1997, vol. 36, pp. 12869-12880.*
NCBI Accession # 540642.*
NCBI Accession # 138800.*
Hildt E. et al, "Characterization of essential domains for the functionality of the MHBst trabscriptional activator and identification of a minimal MHBst activator", ONCOGENE, Bd. 11, Nr. 10, Nov. 16, 1995, Seiten 2055-2066, XP000922823.
Wieprecht T. et al, "Influence of the angle subtended by the positively charged helix face on the membrane activity of amphipathic, antibacterial peptides", BIOCHEMISTRY, Bd. 36, 1997, Seiten 12869-12880, XP002141072 Zusammenfassung.
Oess S. et al, "Novel cell permeable motif derived from the PreS2-domain of hepatitis-B virus surface antigens" Gene Therapy, Bd. 7, Nr. 9, May 2000, Seiten 750-758, XP000922825.
Lehninger, Alfred L., "Principles of Biochemistry", Second Edition, Worth Publishers, New York, NY (1993), p. 113.
Oess et al., "Novel cell permeable motif derived from the PreS2-domain of hepatitis B virus surface antigens" Gene Therapy, vol. 7, pp. 750-758 (2000).

* cited by examiner

*Primary Examiner*—Bruce R. Campell
*Assistant Examiner*—Myron G. Hill
(74) *Attorney, Agent, or Firm*—Olson & Hierl, Ltd.

(57) ABSTRACT

The present invention relates to a cell-permeable polypeptide that can mediate cell permeability to substances, DNA coding for said polypeptide and a method for the production of said polypeptide. The invention also relates to antibodies directed against the polypeptide and the use of said polypeptide in the mediation of cell permeability to substances.

11 Claims, 7 Drawing Sheets

SEQ ID NO: 1  CCC TTA TCG TCA ATC TTC TCG AGG ATT GGG GAC CCT
SEQ ID NO: 2  Pro Leu Ser Ser Ile Phe Ser Arg Ile Gly Asp Pro

FIG. 1

| Subtype ayw (1) | | | | | | | | | | | | |
|---|---|---|---|---|---|---|---|---|---|---|---|---|
| SEQ ID NO: 1 | CCC | TTA | TCG | TCA | ATC | TTC | TCG | AGG | ATT | GGG | GAC | CCT |
| SEQ ID NO: 2 | Pro | Leu | Ser | Ser | Ile | Phe | Ser | Arg | Ile | Gly | Asp | Pro |
| Hydropathy value | -1.6 | 3.8 | -0.8 | -0.8 | 4.5 | 2.8 | -0.8 | -4.5 | 4.5 | -0.4 | -3.5 | -1.6 |
| Subtype ayw (2) | | | | | | | | | | | | |
| SEQ ID NO: 3 | CCC | ATA | TCG | TCA | ATC | TTC | TCG | AGG | ATT | GGG | GAC | CCT |
| SEQ ID NO: 4 | Pro | Ile | Ser | Ser | Ile | Phe | Ser | Arg | Ile | Gly | Asp | Pro |
| Hydropathy value | -1.6 | 4.5 | -0.8 | -0.8 | 4.5 | 2.8 | -0.8 | -4.5 | 4.5 | -0.4 | -3.5 | -1.6 |
| Subtypes adr (1), adr (2), and ayr | | | | | | | | | | | | |
| SEQ ID NO: 5 | CCC | ATA | TCG | TCA | ATC | TTC | TCG | AGG | ACT | GGG | GAC | CCT |
| SEQ ID NO: 6 | Pro | Ile | Ser | Ser | Ile | Phe | Ser | Arg | Thr | Gly | Asp | Pro |
| Hydropathy value | -1.6 | 4.5 | -0.8 | -0.8 | 4.5 | 2.8 | -0.8 | -4.5 | -0.7 | -0.4 | -3.5 | -1.6 |
| Subtype adw, adw2 | | | | | | | | | | | | |
| SEQ ID NO: 7 | CAC | ATC | TCG | TCA | ATC | TCC | GCG | AGG | ACT | GGG | GAC | CCT |
| SEQ ID NO: 8 | His | Ile | Ser | Ser | Ile | Ser | Ala | Arg | Thr | Gly | Asp | Pro |
| Hydropathy value | -3.2 | 4.5 | -0.8 | -0.8 | 4.5 | -0.8 | 1.8 | -4.5 | -0.7 | -0.4 | -3.5 | -1.6 |

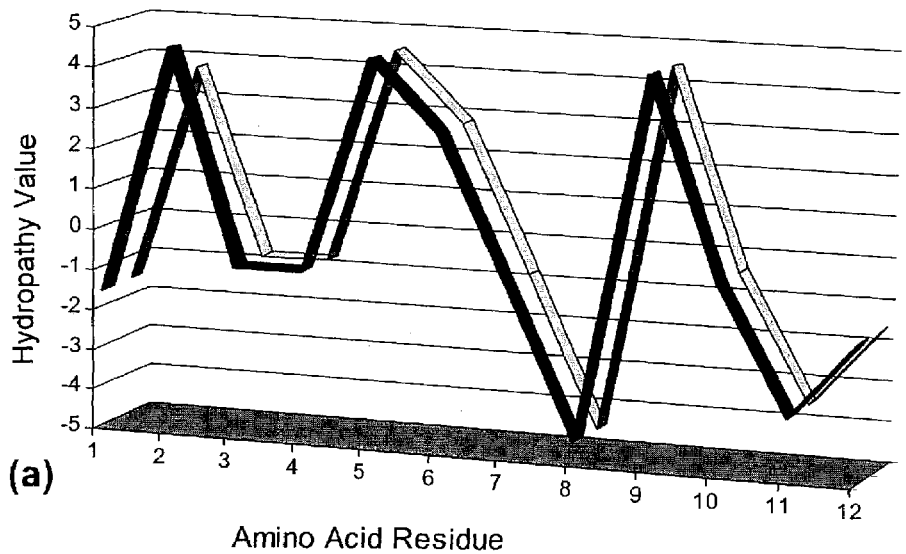

FIG. 3A

| PreS2-TLM | | | | | | | | | | | | |
|---|---|---|---|---|---|---|---|---|---|---|---|---|
| SEQ ID NO: 2 | Pro | Leu | Ser | Ser | Ile | Phe | Ser | Arg | Ile | Gly | Asp | Pro |
| Hydropathy value | -1.6 | 3.8 | -0.8 | -0.8 | 4.5 | 2.8 | -0.8 | -4.5 | 4.5 | -0.4 | -3.5 | -1.6 |
| DHBV3 residues 20-31 | | | | | | | | | | | | |
| SEQ ID NO: 9 | Leu | Leu | Asn | Gln | Leu | Ala | Gly | Arg | Met | Ile | Pro | Lys |
| Hydropathy value | 3.8 | 3.8 | -3.5 | -3.5 | 3.8 | 1.8 | -0.4 | -4.5 | 1.9 | 4.5 | -1.6 | -3.9 |
| DHBV3 residues 42-53 | | | | | | | | | | | | |
| SEQ ID NO: 10 | Thr | Ile | Asp | His | Val | Leu | Asp | His | Val | Gln | Thr | Met |
| Hydropathy value | -0.7 | 4.5 | -3.5 | -3.2 | 4.2 | 3.8 | -3.5 | -3.2 | 4.2 | -3.5 | -0.7 | 1.9 |
| HHBV residues 45-56 | | | | | | | | | | | | |
| SEQ ID NO: 11 | Thr | Ile | Gln | His | Val | Met | Asp | His | Ile | Asp | Ser | Val |
| Hydropathy value | -0.7 | 4.5 | -3.5 | -3.2 | 4.2 | 1.9 | -3.5 | -3.2 | 4.5 | -3.5 | -0.8 | 4.2 |

(a)

(b)

(c)

| | | | | | | | | | | | | |
|---|---|---|---|---|---|---|---|---|---|---|---|---|
| PreS2-TLM | | | | | | | | | | | | |
| SEQ ID NO: 2 | Pro | Leu | Ser | Ser | Ile | Phe | Ser | Arg | Ile | Gly | Asp | Pro |
| Hydropathy value | -1.6 | 3.8 | -0.8 | -0.8 | 4.5 | 2.8 | -0.8 | -4.5 | 4.5 | -0.4 | -3.5 | -1.6 |
| WHV residues 33-44 | | | | | | | | | | | | |
| SEQ ID NO: 12 | Thr | Leu | Ser | Pro | Val | Val | Pro | Thr | Val | Ser | Thr | Ile |
| Hydropathy value | -0.7 | 3.8 | -0.8 | -1.6 | 4.2 | 4.2 | -1.6 | -0.7 | 4.2 | -0.8 | -0.7 | 4.5 |
| GSHV residues 33-44 | | | | | | | | | | | | |
| SEQ ID NO: 13 | Thr | Leu | Ser | Pro | Val | Val | Pro | Thr | Val | Ser | Thr | Thr |
| Hydropathy value | -0.7 | 3.8 | -0.8 | -1.6 | 4.2 | 4.2 | -1.6 | -0.7 | 4.2 | -0.8 | -0.7 | -0.7 |

(a)

SEQUENCE LISTING

<160> NUMBER OF SEQ ID NOS: 13

<210> SEQ ID NO 1
<211> LENGTH: 36
<212> TYPE: DNA
<213> ORGANISM: Hepadnavirus
<220> FEATURE:
<221> NAME/KEY: CDS
<222> LOCATION: (1)...(36)

<400> SEQUENCE: 1 ccc tta tcg tca atc ttc tcg agg att ggg gac cct    36

-continued

```
Pro Leu Ser Ser Ile Phe Ser Arg Ile Gly Asp Pro
 1               5                   10
```

<210> SEQ ID NO 2
<211> LENGTH: 12
<212> TYPE: PRT
<213> ORGANISM: Hepadnavirus

<400> SEQUENCE: 2

```
Pro Leu Ser Ser Ile Phe Ser Arg Ile Gly Asp Pro
 1               5                   10
```

<210> SEQ ID NO 3
<211> LENGTH: 36
<212> TYPE: DNA
<213> ORGANISM: Hepadnavirus
<220> FEATURE:
<221> NAME/KEY: CDS
<222> LOCATION: (1)...(36)

<400> SEQUENCE: 3

```
ccc ata tcg tca atc ttc tcg agg att ggg gac cct         36
Pro Ile Ser Ser Ile Phe Ser Arg Ile Gly Asp Pro
 1               5                   10
```

<210> SEQ ID NO 4
<211> LENGTH: 12
<212> TYPE: PRT
<213> ORGANISM: Hepadnavirus

<400> SEQUENCE: 4

```
Pro Ile Ser Ser Ile Phe Ser Arg Ile Gly Asp Pro
 1               5                   10
```

<210> SEQ ID NO 5
<211> LENGTH: 36
<212> TYPE: DNA
<213> ORGANISM: Hepadnavirus
<220> FEATURE:
<221> NAME/KEY: CDS
<222> LOCATION: (1)...(36)

<400> SEQUENCE: 5

```
ccc ata tcg tca atc ttc tcg agg act ggg gac cct         36
Pro Ile Ser Ser Ile Phe Ser Arg Thr Gly Asp Pro
 1               5                   10
```

<210> SEQ ID NO 6
<211> LENGTH: 12
<212> TYPE: PRT
<213> ORGANISM: Hepadnavirus

<400> SEQUENCE: 6

```
Pro Ile Ser Ser Ile Phe Ser Arg Thr Gly Asp Pro
 1               5                   10
```

<210> SEQ ID NO 7
<211> LENGTH: 36
<212> TYPE: DNA
<213> ORGANISM: Hepadnavirus
<220> FEATURE:
<221> NAME/KEY: CDS
<222> LOCATION: (1)...(36)

<400> SEQUENCE: 7

```
cac atc tcg tca atc tcc gcg agg act ggg gac cct         36
His Ile Ser Ser Ile Ser Ala Arg Thr Gly Asp Pro
```

```
<210> SEQ ID NO 8
<211> LENGTH: 12
<212> TYPE: PRT
<213> ORGANISM: Hepadnavirus

<400> SEQUENCE: 8

His Ile Ser Ser Ile Ser Ala Arg Thr Gly Asp Pro
 1               5                  10

<210> SEQ ID NO 9
<211> LENGTH: 12
<212> TYPE: PRT
<213> ORGANISM: Hepadnavirus

<400> SEQUENCE: 9

Leu Leu Asn Gln Leu Ala Gly Arg Met Ile Pro Lys
 1               5                  10

<210> SEQ ID NO 10
<211> LENGTH: 12
<212> TYPE: PRT
<213> ORGANISM: Hepadnavirus

<400> SEQUENCE: 10

Thr Ile Asp His Val Leu Asp His Val Gln Thr Met
 1               5                  10

<210> SEQ ID NO 11
<211> LENGTH: 12
<212> TYPE: PRT
<213> ORGANISM: Hepadnavirus

<400> SEQUENCE: 11

Thr Ile Gln His Val Met Asp His Ile Asp Ser Val
 1               5                  10

<210> SEQ ID NO 12
<211> LENGTH: 12
<212> TYPE: PRT
<213> ORGANISM: Hepadnavirus

<400> SEQUENCE: 12

Thr Leu Ser Pro Val Val Pro Thr Val Ser Thr Ile
 1               5                  10

<210> SEQ ID NO 13
<211> LENGTH: 12
<212> TYPE: PRT
<213> ORGANISM: Hepadnavirus

<400> SEQUENCE: 13

Thr Leu Ser Pro Val Val Pro Thr Val Ser Thr Thr
 1               5                  10
```

POLYPEPTIDE MEDIATING CELL PERMEABILITY

This application is the National Stage of PCT/DE99/03506, filed Nov. 3, 1999.

The present invention relates to a polypeptide which is cell-permeable and can mediate cell permeability to substances, to a DNA coding for such a polypeptide and a method of producing such a polypeptide. The invention also concerns antibodies directed against the polypeptide and the use of the polypeptide in the mediation of cell permeability to substances.

The property of substances penetrating cells is called cell permeability. This property is, however, only found in few substances. Most substances require auxiliary means and/or methods to penetrate cells. Examples thereof are microinjection, eletroporation, association with cationic lipids, liposome formation, receptor-mediated endocytosis and viral infection. However, these auxiliary means or methods involve great drawbacks. In particular, they are expensive, require complex experimental set-ups and can be used only to a limited extent. Their efficiency degree is also low and they are often toxic.

Therefore, it is the object of the present invention to provide a product by means of which substances can be inserted in cells, the above drawbacks being avoided.

According to the invention this is achieved by the subject matters defined in the claims.

The present invention is based on applicant's insights that a polypeptide comprising preferably the amino acid sequence of FIG. 1 or an amino acid sequence differing therefrom by one or more amino acids may penetrate cells, i.e. has cell permeability. Applicant found such a polypeptide in the PreS2 region of a hepatitis B virus (HBV) surface protein. The polypeptide is referred to below as CPP "cell" permeability-mediating polypeptide. CPP has the structure of an amphiphilic α-helix. Applicant also detected that one of CPP's properties is to mediate cell permeability to substances. The latter may then penetrate cells, the cell permeability of the substances not being limited to certain cells. The substances also retain their activities (cf. FIG. 2). FIG. 3 shows variants of the CPP according to the invention from various HBV subtypes which differ from the sequence of FIG. 1 by one or more amino acids. The amino acid sequence of FIG. 1 (=PreS2–TLM) fully corresponds e.g. to subtype ayw (1) on an amino acid level, whereas the other subtypes have one or more replacements as compared thereto. However, it can be seen that conservation of certain amino acids exists between various HBV subtypes. It can be confirmed in particular by a graphic representation of hydrophobicity values. From this it is possible to draw the conclusion that even if one or more amino acids are replaced, the hydropathy distribution in the whole molecule should be retained. Due to this finding it is easily possible for a person skilled in the art to determine variants of the sequence of FIG. 1, since it is not the sequence as such that is decisive but the hydropathy profile in the whole molecule. The same applies correspondingly to various avian hepadnaviruses (cf. FIG. 4) or hepadnaviruses of rodents (cf. FIG. 5). Each of them is compared with a CPP according to FIG. 1 of the invention (=PreS2-TLM) and hydropathy profiles are prepared. They show that even with an almost complete replacement of the amino acids (e.g. HHBV <- - - >PreS2-TLM) the hydropathy profile is substantially retained. This means that it is not the sequence as such that is decisive but the order of hydrophilic and hydrophobic amino acids in an α-helical motive. In a peptide comprising 12 amino acids, preferably positions 2, 5 and 9 are occupied by hydrophobic amino acids and positions 3, 4, 8, 11 are occupied by hydrophilic amino acids. The hydrophobic amino acids comprise valine, leucine, isoleucine, tryptophan, phenylalanine and methionine. The hydrophilic amino acids include glycine, serine, tyrosine, threonine, cysteine, asparagine and glutamine. A CPP according to the invention thus observes the following general formula:

X o i i o X X i o X i X wherein X=variable amino acid (hydrophilic, hydrophobic or with charged side groups) o=hydrophobic amino acid i=hydrophilic amino acid Amino acids having charged side groups are aspartate, glutamate (both have negatively charged side groups), lysine, asparagine, glutamine, arginine and histidine (all have positively charged side groups).

According to the invention applicant's insights are utilized to provide a polypeptide (CPP) which can mediate cell permeability to substances, CPP comprising the above indicated sequence or preferably the sequence of FIG. 1 or an amino acid sequence differing therefrom by one or more amino acids and being no native HBV surface protein and hybridizing the DNA of the latter amino acid sequence with the DNA of FIG. 1.

The term "mediating cell permeability to substances" refers to the fact that CPP can mediate cell permeability to substances of any kind and origin. The substances may be e.g. polypeptides (proteins), nucleic acids or chemical compounds. Examples of polypeptides are structural polypeptides, tumor necrosis factor, interferons, interleukins, lymphokines, growth factors, plasma proteins, e.g. blood clotting factors and metabolic enzymes, and receptors. In particular, the polypeptides may be those which may increase the immunogenicity of cells. These may be polypeptides not occurring in tumor cells, e.g. cytokines, such as IL-2, and GM-CSF, and co-stimulatory molecules, such as B7-1, tumor-associated antigens, e.g. MAGE1, tyrosinases and viral polypeptides, e.g. E7 of human papilloma virus and EBNA-3 polypeptide of Epstein-Barr virus. The polypeptides may also be adapter polypeptides, oligomerization motives of a polypeptide, polypeptide fragments of viral coat polypeptides, hormones and ribozymes. Examples of nucleic acids are those which may code for the above polypeptides. They may also be antisense oligonucleotides, peptide-nucleic acids and consensus sequences for transcription factors. Examples of chemical compounds are medicaments which have no polypeptide structure. These may be cytostatic agents, anesthetics, antihistaminics, antibiotics and antimycotics. For mediating cell permeability it may suffice to incubate CPP together with a substance so as to form chemical bonds, e.g. covalent or non-covalents bonds. It is favorable for CPP to be linked with the substance via a linker, which may be done e.g. via biotin/streptavidine. The linker may be available at the N-terminus or C-terminus of CPP. It is particularly advantageous for the substance to be present as polypeptide together with CPP in a fusion polypeptide. CPP may in this case be available at the N-terminus or C-terminus or within the polypeptide structure of the substance. Therefore, the term "CPP" also comprises a fusion polypeptide in which CPP is present together with a substance. Mediation of cell permeability to substances may be detected by common methods. It is favorable to incubate cells with CPP-linked substances and detect the penetration or presence of CPP and/or the substances in the cells. This may be done e.g. by specific antibodies or reagents which react directly or indirectly with CPP and/or the substances.

The term "an amino acid sequence differing by one or more amino acids" comprises any CPP-preparing amino acid sequence which is not a native HBV surface protein. A sequence which codes for "an amino acid sequence differing by one or more amino acids" hybridizes preferably with the DNA sequence of FIG. 1. The DNA sequence may differ from the DNA of FIG. 1 by additions, deletions, substitutions and/or inversions of one or more base pairs. The term "hybridization" refers to a hybridization under common conditions, in particular at 20° C. below the melting point of the sequence.

Another subject matter of the present invention is a nucleic acid which codes for CPP. The nucleic acid may be an RNA or a DNA. Preferred is a DNA which comprises the following:
  (a) the DNA of FIG. 1 or a DNA differing therefrom by one or more base pairs, wherein the latter DNA hybridizes with the DNA of FIG. 1 and does not code for a natives HBV surface protein, or
  (b) a DNA related to the DNA of (a) via the degenerated genetic code.

The expression "a DNA differing by one or more base pairs" comprises any DNA sequence coding for a CPP, which hybridizes with the DNA of FIG. 1 and does not code for a native HBV surface protein. The DNA sequence may differ from the DNA of FIG. 1 by additions, deletions, substitutions and/or inversions of one or more base pairs. As to the expression "hybridization" reference is made accordingly to the above explanations.

A DNA according to the invention may be present as such or in a vector. In particular, a DNA according to the invention may be present in an expression vector. Examples thereof are known to the person skilled in the art. In the case of an expression vector for *E. coli* these are e.g. pGEMEX, pUC derivatives, pGEX-2T, pET3b and pQE-8. For the expression in yeast e.g. pY100 and Ycpad1 have to be mentioned while e.g. PKCR, PEFBOS, cDM8, pCEV4, pCDNA3, pKSV10, pRCMV and pRK5 have to be indicated for the expression in animal cells. The bacculovirus expression vector pAcSGHisNT-A is particularly suitable for the expression in insect cells.

The person skilled in the art knows suitable cells to express the DNA according to the invention, present in an expression vector. Examples of such cells comprise the *E. coli* strains HB101, DH1, x1776, JM101, JM 109, BL21, SG 13009 and M15pRep4, the yeast strain *Saccharomyces cerevisiae*, the animal cells L, NIH 3T3, FM3A, CHO, COS, Vero, HeLa, Hep62, CCL13 and 293, the insect cells Sf9 and Sf21 and the plant cells *Lupinus albus*.

The person skilled in the art is familiar with methods and conditions of transforming or transfecting cells with an expression vector containing the DNA according to the invention and culturing the cells. He also knows methods of isolating and purifying the CPP expressed by the DNA according to the invention.

Another subject matter of the present invention is an antibody directed against CPP. Such an antibody may be prepared by common methods. It may be polyclonal or monoclonal. For its preparation it is favorable to immunize with CPP animals—in particular rabbits or chickens for a polyclonal antibody and mice for a monoclonal antibody. Further boosters of the animals may also be made with CPP. The polyclonal antibody may then be obtained from the animal serum or egg yolk. For preparing the monoclonal antibody, animal spleen cells are fused with myeloma cells.

Another subject matter of the present invention is a kit. Such a kit comprises one or more of the following components:
  (a) a cell permeability-mediating polypeptide according to the invention (CPP),
  (b) a DNA according to the invention,
  (c) an antibody according to the invention, and
  (d) common auxiliary agents, such as carriers, buffers, solvents, controls, etc.

One or more representatives of the individual components may be present each. As to the individual terms reference is made to the above explanations.

The present invention enables cell permeability to be mediated. Cell permeability can be mediated to substances of any kind and origin by a CPP according to the invention. The cell permeability is universal, i.e. it is not limited to certain cells. The cells may also be present ex vivo or in vivo. In addition, the cell permeability does not trigger any toxic effects.

The present invention is thus perfectly suited for diagnosis and therapy. The latter comprises influencing the expression of genes and metabolic processes. In particular, the present invention is suited for the diagnosis and therapy of the severest diseases, e.g. of tumors. The present invention distinguishes itself in particular in that it can be used for both conservative and gene-therapeutic measures.

BRIEF DESCRIPTION OF THE DRAWINGS

FIG. 1 shows the amino acid and DNA sequences (SEQ ID NOS.:1 AND 2) of a cell permeability-mediating polypeptide according to the invention (CPP).

FIG. 3 shows the conservation of the amino acid sequence between various HBV subtypes as well as the hydropathy profiles of the HBV subtypes. FIG. 3A (top) provides a table of nucleotide sequences, amino acid sequences and hydropathy values (according to Kyte and Doolittle, 1982) for the PreS2-TLM peptide of HBV subtype ayw (1) (SEQ ID NO: 2) compared to subtypes ayw (2) (SEQ ID NO: 4), adr (1)/adr (2)/ayr (SEQ ID NO: 6), and adw/ adw2 (SEQ ID NO: 8); the amino acid residues and hydropathy values of SEQ ID NO: 2 are shown in bold face, as are the amino acid residues and hydropathy values of SEQ ID NOS: 4, 6 and 8 that are identical to the corresponding residues in SEQ ID NO: 2; panel (a) graphically depicts the hydropathy profile of SEQ ID NO: 4 (in black) compared to SEQ ID NO: 2 (in grey).

FIG. 4 shows amphiphilic motifs in the PreS2 region of various avian hepadnaviruses.

FIG. 5 (top) provides a table of amino acid sequences and hydropathy values (according to Kyte and Doolittle, 1982) for the PreS2 region HBV subtype ayw (1) (SEQ ID NO: 2) compared to WHV residues 33-44 (SEQ ID NO: 12) and GSHV residues 33-44 (SEQ ID NO: 13); panel (a) graphically depicts the hydropathy profile of SEQ ID NO: 13 (in white) and SEQ ID NO: 12 (in black) compared to SEQ ID NO: 2 (in grey). In the graph, the hydropathy values of the amino acid side chains are plotted on the y-axis and the 12 amino acid residues of the peptides are plotted on the x-axis, with the N-terminal amino acid being labeled 1; hydrophobic amino acids have positive hydropathy values and hydrophilic amino acids have negative hydropathy values.

FIG. 6 shows that DHBV42-53-EGFP is a cell-permeable protein.

The present invention is explained by the below examples.

EXAMPLE 1

Detection of Cell Permeability Mediated by a Polypeptide (CPP) According to the Invention The detection of cell permeability mediated by CPP is shown by inhibition of the TNFα-dependent activation of c-Raf1 kinase. The activation of the c-Raf1 kinase is based on the interaction between the TNF receptor I (TNR-RI) and the adapter molecule Grb2. For this purpose, the SH3 domain of Grb2 interacts with a PLAP motive from the cytoplasmic domain of TNF-RI.

CPP is provided in the form of a fusion polypeptide. In this fusion polypeptide referred to as CPP-PLAP CPP, the amino acid sequence of FIG. 1 is present as N-terminus partner and a PLAP motive from the cytoplasmic domain of TNF-RI is present as C-terminus partner. A fusion polypeptide referred to as CPP-KLAP is also provided, which has a mutated PLAP motive.

HeLa cells are incubated for 2 h with 2 μM CPP-PLAP or CPP-KLAP (control) and stimulated for 15 min with 100 μ/ml TNFα. The activation of c-Raf1 kinase is determined by an immunocomplex test using MEK (Santa Cruz, Biotech) and $\gamma^{32}$p-ATP as substrate (cf. FIG. 2).

Figure 2:
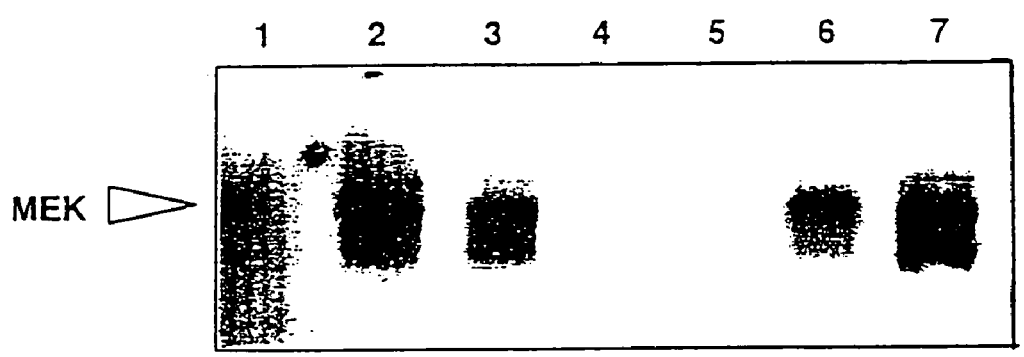
FIG. 2 shows the detection of CPP-mediated cell permeability. Lanes 2 and 3 show the activation of c-Raf1 kinase. Lanes 4 and 5 show the inhibition thereof. Lanes 6 and 7 show that mutated CPP-PLAP (CPP-KLAP) has no inhibitory effect.
Figure 3B:
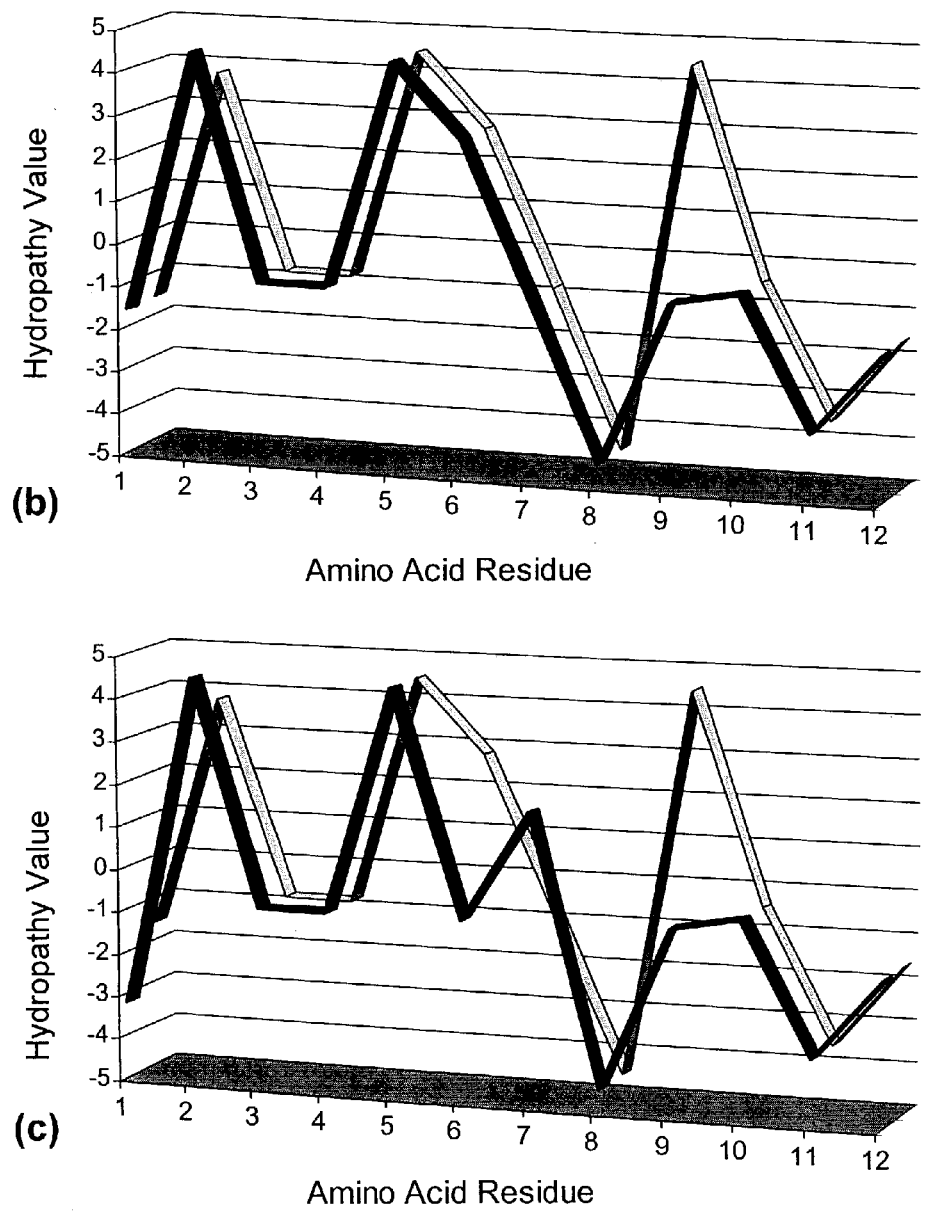
In FIG. 3B, panel (b) graphically depicts they hydropathy profile of SEQ ID NO: 6 (in black) compared to SEQ ID NO: 2 (in grey), and panel (c) graphically depicts the hydropathy profile of SEQ ID NO: 8 (in black) compared to SEQ ID NO: 2 (in grey). In the graphs of FIGS. 3A and 3B, the hydropathy values of the amino acid side chains are plotted on the y-axis and the 12 amino acids residues of the peptides are plotted on the x-axis, with the N-terminal amino acid being labeled 1; hydrophobic amino acids have positive hydropathy values and hydrophilic amino acids have negative hydropathy values.
Figure 4A:
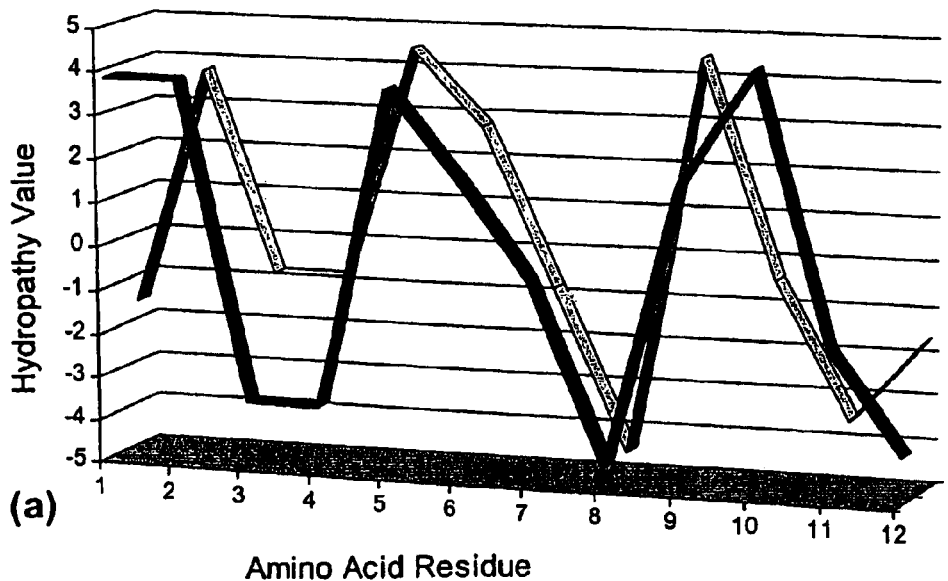
FIG. 4A (top) provides a table of amino acid sequences and hydropathy values (according to Kyte and Doolittle, 1982) for the PreS2 region HBV subtype ayw (1) (SEQ ID NO: 2) compared to DHBV residues 20-31 (SEQ ID NO: 9), DHBV residues 42-53 (SEQ ID NO: 10), and HHBV residues 45-56 (SEQ ID NO: 11); panel (a) graphically depicts the hydropathy profile of SEQ ID NO: 9 (in black) compared to SEQ ID NO: 2 (in grey).
Figure 4B:
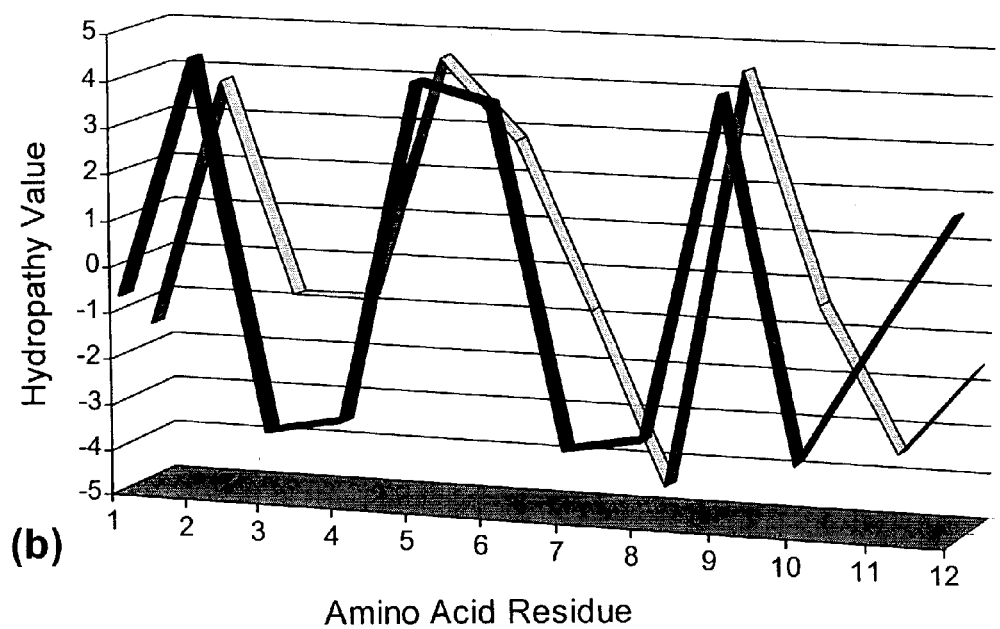
IN FIG. 4B, panel (b) graphically depicts the hydropathy profile of SEQ ID NO: 10 (in black) compared to SEQ ID NO: 2 (in grey), and panel (c) graphically depicts the hydropathy profile of SEQ ID NO: 11 (in black) compared to SEQ ID NO: 2 (in grey). In the graphs of FIG. 4A and 4B, the hydropathy values of the amino acid side chains are plotted on the y-axis and the 12 amino acid residues of the peptides are plotted on the x-axis, with the N-terminal amino acid being labeled 1; hydrophobic amino acids have positive hydropathy values and hydrophilic amino acids have negative hydropathy values.
Figure 4B:
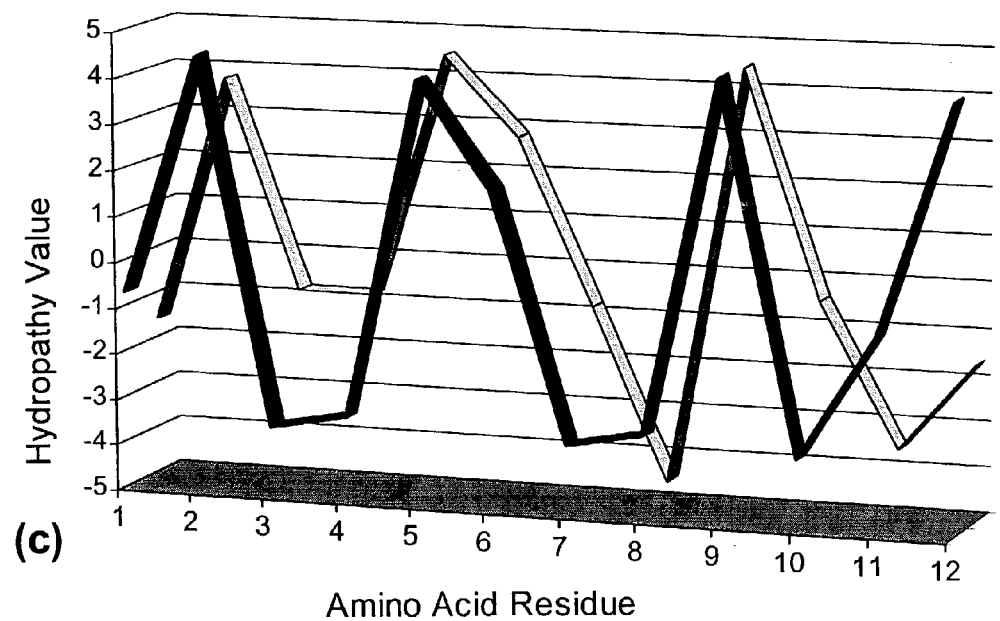
Figure 5:
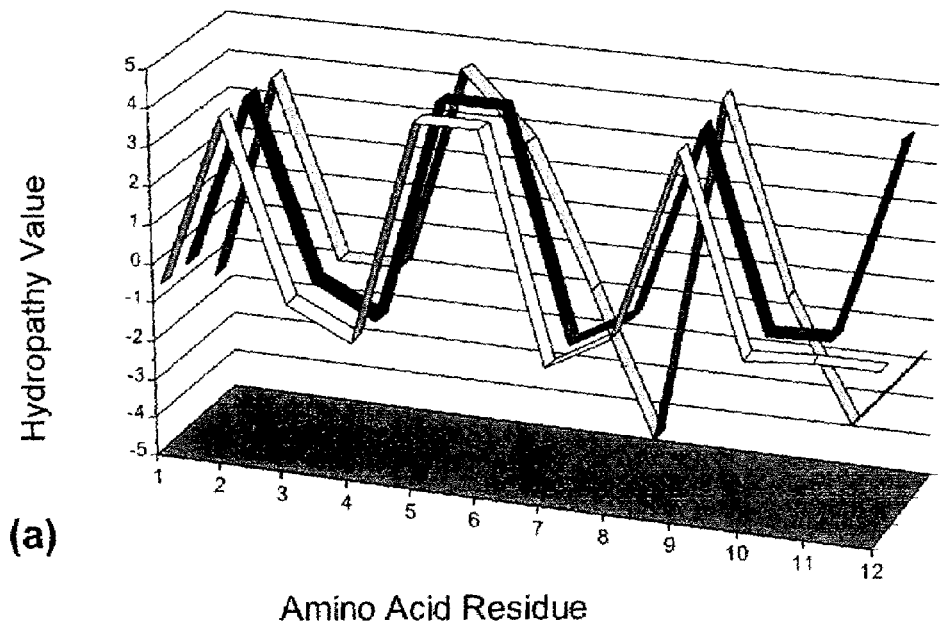
FIG. 5 shows amphiphilic motifs in the PreS2 region of various hepadnaviruses of rodents.

It shows that CPP-PLAP reaches the cells and fully inhibits the activation of C-Raf1 kinase (cf. FIG. 2, lanes 4 and 5). It also turns out that CPP-KLAP does not achieve inhibition (cf. FIG. 2, lanes 6 and 7).

EXAMPLE 2

Preparation and Purification of a Cell Permeability-Mediating Polypeptide (CPP) According to the Invention The DNA of FIG. 1 is provided at the 5' end with a BgIII linker and at the 3' end with a BamHI linker and is subsequently cleaved with the corresponding restriction enzymes. The resulting BgIII/BamHI fragment is inserted in the BamHI-cleaved expression vector pQe8 so as to obtain the expression plasmid pQe8/CPP.

One sequence coding for GST (glutathione S transferase) is also isolated from the expression plasmid pGex-1. At its 5' end it has a BamHI restriction site followed by a sequence coding for a thrombin restriction site. At its 3' end the sequence has a BamHI restriction site. The sequence is inserted in the BamHI-cleaved expression plasmid pQe8/CPP so as to obtain the expression plasmid pQe8/CPP-GST. It codes for the fusion polypeptide CPP-GST, pQe48/CPP-GST is used for the transformation of *E. coli* SG 13009 (cf. Gottesmann, S. et al., J. Bacteriol. 148 (1981), 265-273). The bacteria are cultured in an LB broth with 100 μg/ml ampicillin and 25 μg/ml kanamycin and induced for 4 h with 60 μM isopropyl-β-D-thiogalactopyranoside (IPTG). Following induction, lysis of the sedimented and washed bacteria is carried out by means of ultrasound. The CPP-GST fusion polypeptide is isolated by means of affinity chromatography on a glutathione column. The bound CPP-GST fusion polypeptide is eluted from 0 to 10 mM by means of a linear increase in the glutathione concentration. The eluted CPP-GST fusion protein is subjected to thrombin cleavage. The hexa-His-CPP (fusion polypeptide) released in this way is subsequently isolated by affinity chromatography using denaturing conditions by means of an Ni-NTA agarose. This is done in the presence of 6 M urea in accordance with the instructions from the manufacturer (Quiagen company). The bound hexa-His-CPP is eluted in a buffer having pH 6.3, containing 250 mM imidazole. The hexa-His-CPP is subjected to 18% SDS polyacrylamide gel electrophoresis and stained using coomassie blue (cf. Thomas, J. O. and Kornberg, R. D., J. Mol. Biol. 149 (1975), 709-733).

It shows that a (fusion) polypeptide according to the invention can be prepared in highly pure form.

EXAMPLE 3

Preparation and Detection of an Antibody According to the Invention

A fusion polypeptide of Example 2 according to the invention is subjected to 18% SDS polyacrylamide gel electrophoresis. After staining the gel with 4 M sodium acetate, an about 3 kD band is excised out of the gel and incubated in phosphate-buffered common salt solution. Gel pieces are sedimented before the protein concentration of the supernatant is determined by SDS polyacrylamide gel electrophoresis followed by coomassie blue staining. Animals are immunized as follows with the gel-purified fusion polypeptide.

Immunization Protocol for Polyclonal Antibodies in Rabbits

35 μg of gel-purified fusion polypeptide in 0.7 ml PBS and 0.7 ml of complete or incomplete Freund's adjuvant are used per immunization:

Day 0: 1ˢᵗ immunization (complete Freund's adjuvant)
Day 14: 2ⁿᵈ immunization (incomplete Freund's adjuvant; icFA)
Day 28: 3ʳᵈ immunization (icFA)
Day 56: 4ᵗʰ immunization (icFA)
Day 80: bleeding to death.

The rabbit serum is tested in an immunoblot. For this purpose, a fusion polypeptide of Example 2 according to the invention is subjected to SDS polyacrylamide gel electrophoresis and transferred to a nitrocellulose filter (cf. Khyse-Andersen, J., J. Biochem. Biophys. Meth. 10 (1984), 203-209). The Western blot analysis was carried out as described in Bock, C.-T. et al., Virus Genes 8, (1994), 215-229. For this purpose, the nitrocellulose filter is incubated with a first antibody at 37° C. for one hour. This antibody is the rabbit serum (1:10000 in PBS). After several wash steps using PBS, the nitrocellulose filter is incubated with a second antibody. This antibody is an alkaline phosphatase-coupled monoclonal goat anti-rabbit IgG antibody (Dianova company) (1:5000) in PBS. 30 minutes of incubation at 37° C. are followed by several wash steps using PBS and subsequently by the alkaline phosphatase detection reaction with developer solution (36 µM 5'-bromo-4-chloro-3-indolylphosphate, 400 µM nitro blue tetrazolium, 100 mM Tris-HCl, pH 9.5, 100 mM NaCl, 5 mM MgCl$_2$) at room temperature until bands are visible.

It shows that polyclonal antibodies according to the invention can be prepared.

Immunization Protocol for Polyclonal Antibodies in Chickens

40 µg of gel-purified fusion polypeptide in 0.8 ml PBS and 0.8 ml of complete or incomplete Freund's adjuvant are used per immunization.
Day 0: 1ˢᵗ immunization (complete Freund's adjuvant)
Day 28: 2ⁿᵈ immunization (incomplete Freund's adjuvant; icFA)
Day 50: 3ʳᵈ immunization (icFA)

Antibodies are extracted from egg yolk and tested in a Western blot. Polyclonal antibodies according to the invention are detected.

Immunization Protocol for Monoclonal Antibodies in Mice

12 µg of gel-purified fusion polypeptide in 0.25 ml PBS and 0.25 ml of complete or incomplete Freund's adjuvant are used per immunization. In the fourth immunization, the fusion protein is dissolved in 0.5 ml (without adjuvant).

| Day 0:  | 1st immunization (complete Freund's adjuvant) |
| Day 28: | 2nd immunization (incomplete Freund's adjuvant; icFA) |
| Day 56: | 3rd immunization (icFA) |
| Day 84: | 4th immunization (PBS) |
| Day 87: | fusion |

Supernatants of hybridomas are tested in a Western blot. Monoclonal antibodies according to the invention are detected.

EXAMPLE 4

Detection of the Cell Permeability Mediated by DHBV-CPP

Detection of the cell permeability mediated by DHBV (duck hepatitis B virus)-CPP was made as follows: According to standard methods a fusion protein consisting of a hexa-His-Tag (6H), DHBV-CPP and eGFP (enhanced green fluorescent protein) was prepared in analogy to Example 1 in an *E. coli* expression system. The pQE vector system of the Quiagen company was used. This protein (DHBV42-53eGFP) was isolated. wt6HeGFP (fusion protein of 6 His and eGFP) was used for control experiments. Then, 293 cells were incubated in the presence of these proteins for 10 and 20 minutes. The proteins were added to the medium at a concentration of 1 µM. After 10 or 20 minutes, the cells were lyzed and the cytosolic fraction of the cells was isolated by ultracentrifugation.

The presence of DHBV42-53 eGFP in the cytosol fraction was detected by means of Western blot analysis using a hexa-His-tag-specific antibody (FIG. 6, lanes 1-4) (anti-hexa-His6 of Qiagen company) or an eGFP-specific antibody (anti-eGFP of Clontech company) (FIG. 6, lanes 5-8). A peroxidase-conjugated secondary antibody (anti-mouse HRP, anti-rabbit-HRP of Amersham company) was used for the detection.

The Western blot shows that when DHBV42-53-eGFP is added an internalization of the protein into the cell (cytosol) can be observed after 10 min. (lanes 2, 6) or 20 minutes (4, 8) whereas in the case of the control protein wt6HeGFP which lacks the sequence mediating cell permeability this cannot be observed after either 10 minutes (lanes 1, 5) or 20 minutes (lanes 3, 7).

These results show that DHBV-CPP is capable of acting as a carrier for other proteins.

What is claimed is:

1. An isolated oligopeptide consisting of 12 amino acid residues and having an amino acid residue sequence selected from the group consisting of SEQ ID NO: 2, SEQ ID NO: 4, SEQ ID NO: 6, SEQ ID NO: 8, SEQ ID NO: 9, SEQ ID NO: 10, SEQ ID NO: 11, SEQ ID NO: 12, and SEQ ID NO: 13.

2. A fusion protein comprising a polypeptide covalently linked to an oligopeptide of claim 1; wherein the fusion protein is not a natural hepatitis B virus surface protein.

3. The fusion protein of claim 2 wherein the polypeptide is selected from the group consisting of a structural polypeptide, a tumor necrosis factor, an interferon, an interleukin, a lymphokine, a growth factor, and a plasma protein.

4. The fusion protein of claim 2 wherein the polypeptide is a cytokine.

5. The fusion protein of claim 2 wherein the polypeptide is a co-stimulatory molecule.

6. The fusion protein of claim 2 wherein the polypeptide is a tumor-associated antigen.

7. The fusion protein of claim 2 wherein the polypeptide is a peptide fragment of a viral coat.

8. The fusion protein of claim 2 wherein the polypeptide is a hormone.

9. An isolated variant of the peptide of SEQ ID NO: 2, the variant consisting of 12 amino acid residues and having an amino acid residue sequence selected from the group consisting of SEQ ID NO: 4, SEQ ID NO: 6, and SEQ ID NO: 8.

10. An isolated oligopeptide fragment of an avian hepadnavirus, the oligopeptide consisting of 12 amino acid residues and having an amino acid residue sequence selected from the group consisting of SEQ ID NO: 9, SEQ ID NO: 10, and SEQ ID NO: 11.

11. An isolated oligopeptide fragment of a rodent hepadnavirus, the oligopeptide consisting of 12 amino acid residues and having an amino acid residue sequence selected from the group consisting of SEQ ID NO: 12 and SEQ ID NO: 13.

* * * * *